United States Patent [19]

Cheng

[11] Patent Number: 4,767,626

[45] Date of Patent: Aug. 30, 1988

[54] REMEDY FOR ANEMIA AND ARTHRITIS

[76] Inventor: Theodore Cheng, 1209 W. Wynnewood Rd., Wynnewood, Pa. 19096

[21] Appl. No.: 836,204

[22] Filed: Feb. 27, 1986

Related U.S. Application Data

[63] Continuation-in-part of Ser. No. 710,628, Mar. 11, 1985, abandoned.

[51] Int. Cl.⁴ .................... A61K 35/78; A61K 31/56; A61K 31/335; A61K 31/34
[52] U.S. Cl. .................. 424/195.1; 514/182; 514/463; 514/468; 514/469; 514/814; 514/825
[58] Field of Search .................. 424/195.1; 514/182, 514/281, 291, 463, 469, 468, 814, 825

[56] References Cited

U.S. PATENT DOCUMENTS

| | | | |
|---|---|---|---|
| 89,039 | 4/1869 | Gainn | 424/195.1 |
| 166,823 | 8/1875 | Sullivan | 424/195.1 |
| 211,477 | 1/1879 | Sailvail | 424/195.1 |
| 241,014 | 5/1881 | Holland | 424/195.1 |
| 329,697 | 11/1885 | Barr | 424/195.1 |
| 351,829 | 11/1889 | Davis | 424/195.1 |
| 378,156 | 2/1888 | Whitney | 424/195.1 |
| 3,317,386 | 5/1967 | Humble | 424/195.1 |

OTHER PUBLICATIONS

E. Steen, et al., Anatomy and Physiology, vol. 1, 1959, p. 215.
Noer, JAMA, 197:117–122, 1966.
Stein et al., Arthritis and Rheumatism, 23:206–210, 1980.
Martenis et al., Arthritis and Rheumatism, 11:683–687, 1968.
Beisel, Ann. Rev. of Med., 1975, pp. 9 and 13.
Remington, Pharm. Sci., 15th Ed., 1975, pp. 1277, 1278.

*Primary Examiner*—John Rollins
*Attorney, Agent, or Firm*—Steele, Gould & Fried

[57] ABSTRACT

A method for the treatment of anemia associated with viral and bacterial infection in a patient wherein symptoms of rheumatoid arthritis are present, by administering to the patient an effective amount of a composition capable of increasing thyroxine in the blood stream of said patient and thereby increasing stem cells in the blood stream. The composition preferably comprises fat soluble alkaloid extracts from the root of Zanthoxylum Simulans.

4 Claims, No Drawings

REMEDY FOR ANEMIA AND ARTHRITIS

The present application is a continuation-in-part of application Ser. No. 710,628, filed Mar. 11, 1985, now abandoned.

FIELD OF THE INVENTION

The present invention relates to a method and composition for the alleviation of certain symptoms associated with rheumatoid arthritis. Also, the present invention is concerned with a method for diagnosing and monitoring patients suffering from rheumatoid arthritis. More particularly, the present invention relates to the treatment of anemia associated with rheumatoid arthritis. A still further part of the invention is the treatment of anemia which results from bacterial or viral infections and indicates also the presence of arthritis.

BACKGROUND OF THE INVENTION

There have been a number of investigations which indicate that certain bacterial and viral infections contribute to a subsequent development of the syndrome of rheumatoid arthritis as well as mild anemia. Some of these reports have indicated that there is a high incidence of anemia in patients which are suffering from rheumatoid arthritis. Such anemia is characterized as being moderately hypochromic and normocytic.

Freireich et al, in the article entitled "Radioactive Iron Metabolism & Erythrocyte Studies of the Mechanism of the Anemia Associated With Rheumatoid Arthritis", J. Clinical Investigation 36: 1055 (1957), reported the mechanism of said anemia in arthritic patients, appears to be the rate of said red cell destruction was increased while the rate of said red cell synthesis was comparable to normal. Said anemia results because erythropoiesis fails to increase in order to compensate for said increased rate of red cell destruction. Said erythropoiesis, includes the synthesis of stem cells maturing into red blood cells in the bone marrow and in said blood stream with its continuous division and differentiation, appears to be self-regulating and also under the influence of thyrotropin, a thyroid hormone.

Harris et al, in the article entitled "The Red Cell", Harvard University Press, Cambridge, Mass. 1972, page 737, noted said anemia associated with active rheumatoid arthritis appears to belong in the same general category as the anemia secondary to chronic infection or inflammation.

Harvey et al, in the article entitled, "Anemia Associated With Rheumatoid Diseases", Arthritis and Rheumatism, 26: 28 (1983), noted said mild anemia associated with arthritis, is the most commonly reported extra-articular manifestation of rheumatoid arthritis, yet its pathogenesis remains unclear.

Gray et al, in an article entitled, "Alkaloid, Lignan and Sterol Constituents of Zanthoxylum Simulans", Planta Medica, Vol. 39, no. 3, July 1980, page 209, which is incorporated herein by reference, describes the extraction and identification of some of the constituents of Zanthoxylum Simulans.

Gray et al found the major alkaloid in Zanthoxylum Simulans, was chelerythrine with smaller quantities of dihydro- and oxy-chelerythrine, N-acetylanomine, skimmianine, fagarine, sitosterol and sesamine. Another alkaloid was obtained as an oil, molecular formula $C_{16}H_{17}O_3N$, $M+271.1211$. Spectral characteristics were in accord with those of the angular pyranoquinoline alkaloid 8-methoxy-N-methylflindersine previously synthesized by Hifhawy et al. A dried root bark sample was Soxhlet extracted with light petroleum $CHCl_3$ which yielded chelerythrine and then MeOH which gave candicine, sucrose and traces of magnoflorine.

Gray et al, in an article entitled "Alkaloids and Coumarins from North American Zanthoxylum Species", Lloydia, Vol. 38, 1975, pages 268-270, which is incorporated herein by reference, describes an extraction procedure for root and stem barks of Zanthoxylum species.

To date, the treatment of rheumatoid arthritis has been directed to the alleviation of the inflammation of the joints by the administration of the different anti-inflammatory drugs, including aspirin, ibuprofen, indometacin, phenylbutazone, fenoprofen, diclofenac, sulindac, tolmetin, corticosteroids, etc. Monitoring of the disease has been primarily with respect to the amount of inflammation and pain present. Treatment of the associated anemia by the administration of iron has been found to be ineffective either by oral iron or injected iron. It is well known that injected iron is eliminated more rapidly from the plasma space in patients with rheumatoid arthritis than in healthy persons.

SUMMARY OF THE INVENTION

The present invention relates to a method for the treatment of anemia which is associated with rheumatoid arthritis and of the anemia present in patients having a viral or bacterial infection wherein symptoms of rheumatoid arthritis are additionally present. According to the invention, the associated anemia which is characterized as being moderately hypochromic and normocytic is treated by administering to a patient in need of treatment a composition for increasing the thyroxine in the blood stream and thereby increasing the ceiling on the number of red cells maturing from the stem cells in the blood stream. The composition can include the presence of an anti-inflammatory agent so as to treat the inflammation present and reduce any pain.

This invention also relates to a composition and method for treating the mild anemia which occurs during a severe illness caused by the body defense system inactivating by way of the hypothalamus. In such cases, the negative feedback of the pituitary-thyroid's tight control of the red blood cell level falls below normal and remains so even after recovery of the original severe illness, thus causing reduced oxygen supply to the various tissues with vital organs claiming priority.

In accordance with one embodiment of the invention, a composition comprising the fat soluble alkaloid extracts from the root of Zanthoxylum Simulans is utilized for the treatment of the anemia. Such a composition has been found to be effective for re-activating by way of the hypothalamus, the negative feedback pituitary-thyroid tight control of the red blood cell level and thus removing the mild anemia after severe illness. The extract can be either administered alone or in combination with a suitable anti-inflammatory agent.

The extract from the foot of said Zanthoxylum Simulans has now been found to be most effective in alleviating the mild anemia lingering after an acute illness and the mild anemia associated with said rheumatoid arthritis. The Chinese people like the flavor of said Zanthoxylum Simulans seeds, berries, leaves and bark and use said berries to strongly flavor pork in their diet. The long and widespread use of the extract in China has shown the extract to be safe for human consumption.

In accordance with another feature of the invention there is provided a method for treating rheumatoid arthritis and the associated anemia by the administration of thyroidal stimulating compounds including thyroidal extracts, tyrosine, and the like. Preferably, the thyroidal stimulation compounds are administered together with a suitable anti-inflammatory agent.

It is an object of the present invention to provide a method and a composition for the treatment of anemia associated with bacterial and viral infections.

It is a further object of the invention to provide a method and composition for the treatment of anemia associated with rheumatoid arthritis.

It is a yet further object of the invention to provide a method and composition for the treatment of anemia by providing a means for increasing the thyroxide in the blood of a patient in need of such treatment.

The dose required depends upon the clinical circumstances in each case and the particular medicaments being utilized. Where the medicament comprises thyroidal extracts, tyrosine, and the like, a series of doses each of 10–100 mg of the effective ingredient may be required. The anti-inflammatory agents can be administered together or separately from the thyroidal stimulating compounds.

When the medicament administered is the extract of Zanthoxylum Simulans, an effective amount has been found to be about 15–40 g, preferably about 30 g, administered weekly over about a three week period, on a daily basis, preferably in unit dosage from and depending upon the severity of the anemia.

The extract of Zanthoxylum Simulans has been found to be the preferred medicament because of its absence of any noticable side effects and lack of irritation to the gastrointestinal tract. Moreover, the extract has been found to help alleviate the gastrointestinal irritations which may occur through the use of the anti-inflammatory agents when coadministered. Therefore, it is advantageous to administer the anti-inflammatory agents together with the extract.

The following examples serve to demonstrate the compositions and preparations of the invention.

EXAMPLE 1

Preparation of Extract

Root- and stem-barks, leaves and berries of Zanthoxylum Simulans was milled and 150 g. of the milled product were extracted in a Soxhet apparatus with 3 l of methanol. The mixture was concentrated to dryness and dark crystals were obtained.

The crystals from part A were dissolved in petrol extract and chromatographed on 1 mm layers of Sigel using mixtures of n-hexane and ethyl acetate. Separate fractions were separated and identified by UV and IR. The separate fractions were identified as containing as a major fraction chelerythrine and minor amounts of dihydrochelerythrine, oxychelerythrine, N-acetylanomaine, skimmianine, fagarine, sisosterol and sesamin and 8-methoxy-N-methyl-flendersine.

EXAMPLE 2

An elixir is prepared by admixing the following:

| Extract of Example 1 | 50 g |
| Ethanol | 10 ml |
| 70% aqueous sorbitol solution | 50 g |
| Sodium carboxymethyl cellulose 400 cp/2% | 6 g |
| Sodium salt of saccharin | 2 g |
| Anethole · | 0.2 g |
| Water | 50 g |

If desired an anti-inflammatory agent may be added to the mixture. The addition of about 2% by weight of composition of the anti-inflammatory agent preferably, ibuprofen is advantageous to treat the combined symptoms of anemia and the inflammation of the joints.

EXAMPLE 3

1.43 g of indometacine and 1.0 g of tyrosine are dissolved in 50 ml of heated ethanol. The ethanol is then separated by distillation. The remaining substance is mixed with suitable additives pressed into pills or filled into capsules.

EXAMPLE 4

| Acetyl salicylic acid | 216 mg |
| Thyroid extract | 100 mg |
| Aerosil | 50 mg |
| Na—caboxymethylcellulose | 16 mg |
| Cuttina H | 12 mg |
| Microcrystalline cellulose | 150 mg |

The substances listed above are mixed, pressed and the items so pressed are coated in a manner known per se with 20 mg of hydroxypropylmethylcellulose phthalate in a coating drum.

The principals, preferred embodiments and modes of operation of the present invention have been described in the foregoing specification. The invention which is intended to be protected herein, however, is not to be construed as limited to particular forms disclosed, since these are to be regarded as illustrative rather than restrictive. Variations and changes may be made by those skilled in the art without departing from the spirit of the invention.

What is claimed is:

1. A method for the treatment of anemia associated with viral and bacterial infection in a patient wherein symptoms of rheumatoid arthritis are present which comprises administering to said patient an effective amount of a fat soluble alkaloid extract from Zanthoxylum Simulans.

2. The method of claim 1 wherein said extract comprises alkaloids selected from the group consisting of chelerythrine, dihydrochelerythrine, oxychelerythrine, skimmianine, fagarine, sistosterol and sesamine.

3. A composition for the treatment of anemia associated with viral and bacterial infection in a patient wherein symptoms of rheumatoid arthritis are present, which comprise an effective amount of a fat soluble alkaloid extract from Zanthoxylum Simulans and a suitable carrier.

4. The composition of claim 3 wherein said extract comprises alkaloids selected from the group consisting of chelerythrine, dihydrochelerythrine, oxychelerythrine, skimmianine, fagarine, sistosterol and sesamine.

* * * * *